Figure 2:
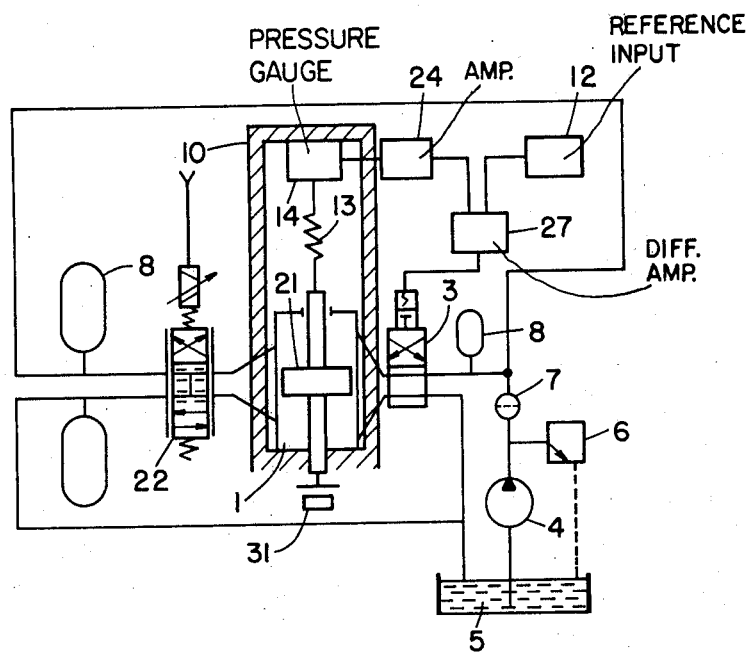

United States Patent [19]

Lechner et al.

[11] 4,283,956
[45] Aug. 18, 1981

[54] METHOD OF DETECTING THE ONSET OF CRACKING IN ARTICLES DURING DYNAMIC TESTING

[75] Inventors: Karl Lechner, Gröbenzell; Erich Bösmiller, Unterschleissheim, both of Fed. Rep. of Germany

[73] Assignee: Motoren-und Turbinen-Union, Fed. Rep. of Germany

[21] Appl. No.: 37,710

[22] Filed: May 10, 1979

[30] Foreign Application Priority Data

May 17, 1978 [DE] Fed. Rep. of Germany ....... 2821553

[51] Int. Cl.³ .............................................. G01N 3/36
[52] U.S. Cl. ......................................... 73/799; 73/577
[58] Field of Search .......................... 73/799, 579, 577

[56] References Cited

U.S. PATENT DOCUMENTS

| 3,228,238 | 1/1966 | Jentet ................................. 73/577 X |
| 3,442,120 | 5/1969 | Russenberger et al. ........... 73/577 X |

FOREIGN PATENT DOCUMENTS 591747  2/1978  U.S.S.R. ................................... 73/799

Primary Examiner—Jerry W. Myracle
Attorney, Agent, or Firm—Scully, Scott, Murphy & Presser

[57] ABSTRACT

A method is disclosed for detecting the onset of cracking in an article subjected to dynamic loading. The article is subjected to a dynamically changing load, and additionally is loaded and vibrated at its natural frequency. The onset of a crack in the article is determined by noting a change in its natural frequency.

7 Claims, 2 Drawing Figures

METHOD OF DETECTING THE ONSET OF CRACKING IN ARTICLES DURING DYNAMIC TESTING

The present invention relates to a method of detecting the onset of cracking in articles (e.g. machine components) during dynamic testing of materials.

During dynamic strength testing of articles or components, it is necessary for determining the low cycle fatigue to determine the number of load cycles at which cracking occurs as well as at which fracture occurs. There are difficulties in determining the number of load cycles at which cracking occurs. Usually the crack can only be seen optically when it has already reached large dimensions. Other known methods of detecting cracks, such as by means of ultrasonics or by means of passing a current through the article, require considerable technical expenditure and are of very limited use if the testing is to be carried out at elevated temperatures.

An object of the present invention is therefore to provide a method of detecting cracking which requires considerably less technical expense, and offers greater reliability even when carried out at higher temperatures. Passing current through the article under test, as well as optical scanning, is to be avoided.

The invention provides a method of detecting the onset of cracking in an article subjected to dynamic loading, wherein the article is loaded and vibrated at its natural frequency, and the onset of a crack is determined by noting a change in the natural frequency.

The testing for the onset of cracking normally takes place in an hydropulser, which is a so-called two-mass oscillator. The article under test thus acts as a spring with a spring constant C, and a loading piston on one side, and the housing or the frame of the testing machine on the other side, constitute the two masses. This two-mass system has different natural frequencies. The basic frequency $f_0$ is only dependent on the spring constant of the article, since the masses of the testing machine (working piston and housing) remain constant. If the article begins to crack during dynamic testing, then the spring constant changes and there is a new natural frequency $f_1$. The change in natural frequency $\Delta f = f_0 - f_1$ is a measure of the beginning of cracking or the dimensions of the crack. The natural frequency is easily recognizable as the resonance frequency as a result of the large amplitude ratios (amplitude of excitation to the increased amplitude).

The measuring of the self-adjusting natural frequency is carried out preferably with constant bias conditions of the article, so that errors arising from different output conditions can be safely avoided.

It is particularly advantageous if the measuring of the self-adjusting natural frequency is carried out at zero load. Measuring can however also be carried out at zero extension of the article.

A particularly advantageous method of exciting the article to its natural frequency is directly by means of a servo valve of a dynamic material testing machine. Such a method of excitation is to be recommended particularly for relatively high masses and relatively small spring constants of the two-mass system (low natural frequency). If the masses are relatively small and the spring constant is relatively high, then it is preferable to provide additionally a high-frequency servo valve near the servo valve which controls the pulsing of the dynamic material testing machine, and to excite the oscillating system with the natural frequency via this high-frequency servo valve.

The article can however also advantageously be excited by means of an electro-magnetic oscillator which operates on the working piston of the dynamic material testing machine. This form of excitation is particularly suitable if very high frequencies of excitation are required.

Figure 1:
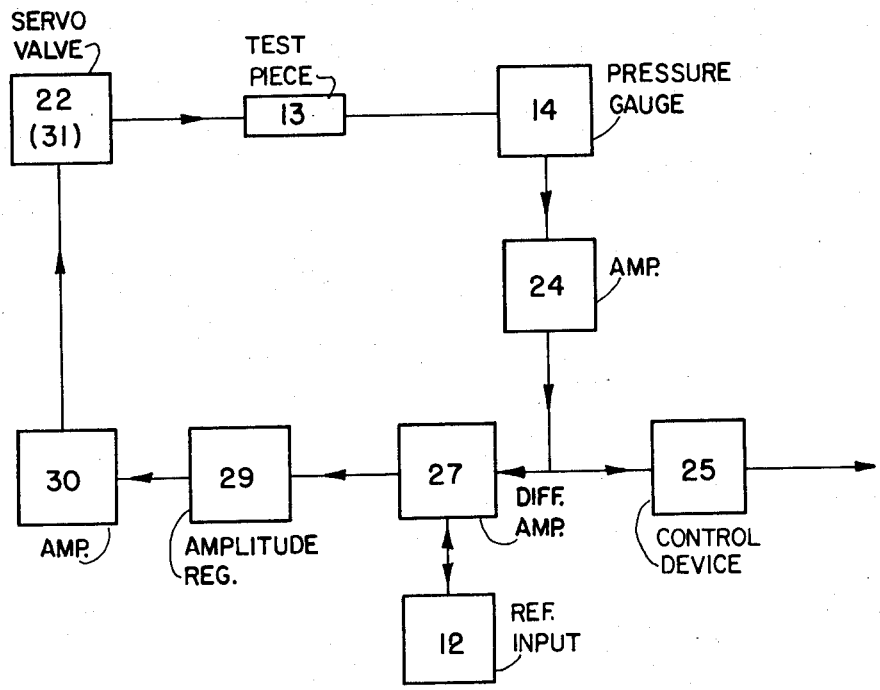

An embodiment according to the invention will now be described with reference to the accompanying drawings, wherein, FIG. 1 is a block diagram of a circuit for supplying the frequency of excitation and registering the natural frequency of an article in a dynamic material testing machine, and FIG. 2 shows schematically an hydropulser in which the method according to the invention can be carried out.

An hydropulser shown schematically in FIG. 2 comprises a housing 10 containing a working cylinder 1 with a working piston 21 arranged therein. A dynamically-changing load is applied to an article or a test piece 13, which is shown as a spring, via the piston 21. An electrohydraulic servo valve 3 controls the flow of oil to the cylinder 1, which produces the desired testing load on the test piece 13. This testing load is measured in a pressure gauge 14, and is converted into an electrical voltage proportional to the test load and amplified in a test amplifier 24. This voltage is compared in a variable-gain amplifier 27 with the reference input from a setting means 12. If there is a difference between the theoretical and actual values, the electrical current required to operate the servo valve is produced in the variable-gain amplifier 27 by means of circuits and a power amplifier. The components 3, 1, 13, 14, 24 and 27 form a closed-loop control system. Energy is supplied by an hydraulic control unit comprising components 4–8.

The system is excited at its natural frequency either by means of the servo valve 3, or by means of an additional high-frequency servo valve 22, or by means of an electro-magnetic oscillator 31 connected to the piston 21.

The natural frequency is reached by means of a circuit shown in FIG. 1 which also registers any change in the natural frequency. The test piece is again indicated by 13, the high-frequency exciter by 22 or 31, the pressure gauge by 14 and a test amplifier subsequently added to the pressure gauge, by 24. A comparator 27 of the theoretical and actual values, including a resonance-dwell system, compares the frequency of the amplifier 24 with the theoretical frequency from the setting means 12. The comparator gives the exact adjustment of the natural frequency of the test piece 13, or of the two-mass system. The control voltage from the comparator is fed via an amplitude regulator 29 and a further amplifier 30 to the high-frequency control member (either the hydraulic servo valve 22 or an electro-magnetic oscillator 31).

If the test piece 13 cracks, the natural frequency changes and this is registered by a control device 25. This control device 25 can be very sensitively adjusted, so that even with a small drop in frequency from the amplifier 24 the control device 25 emits a signal which, e.g. can be used to disconnect the hydropulser, or can be detected or recorded in other ways.

What we claim is:

1. A method of detecting the onset of cracking in an article subjected to dynamic loading, including subjecting the article to a dynamically changing load, and additionally loading and vibrating the article at its natural frequency, and determining the onset of a crack by noting a change in the natural frequency.

2. A method as claimed in claim 1, wherein the natural frequency is always measured at the same load.

3. A method as claimed in claim 2, wherein the natural frequency is measured at zero test load.

4. A method as claimed in claim 1, 2 or 3, wherein the article is excited at its natural frequency by feeding this excitation frequency via the servo valve of a dynamic material testing machine.

5. A method as claimed in claim 4, wherein the article is excited at its natural frequency by means of an additional high-frequency servo valve.

6. A method as claimed in claim 1, 2 or 3, wherein the article is excited at its natural frequency by means of an electro-magnetic oscillator, which acts on a loading piston of a dynamic material testing machine.

7. A method as claimed in claim 6, wherein the article is excited at its natural frequency by means of an additional high-frequency servo valve, which superimposes the natural frequency of the test frequency of the piston.

* * * * *